United States Patent [19]

Bedding et al.

[11] Patent Number: 5,554,533
[45] Date of Patent: Sep. 10, 1996

[54] APPARATUS AND METHOD FOR REARING NEMATODES, FUNGI, TISSUE CULTURES AND THE LIKE, AND FOR HARVESTING NEMATODES

[75] Inventors: Robin A. Bedding, Flynn; Michael A. Stanfield, Tasmania; Graham W. Crompton, Grenfell, all of Australia

[73] Assignee: Commonwealth Scientific and Industrial Research Organisation, Campbell, Australia

[21] Appl. No.: 411,078

[22] Filed: Mar. 27, 1995

Related U.S. Application Data

[63] Continuation of Ser. No. 955,899, Dec. 11, 1992, abandoned.

[30] Foreign Application Priority Data

Apr. 11, 1990 [AU] Australia ................... PJ9571

[51] Int. Cl.$^6$ ............................................. C12N 1/12
[52] U.S. Cl. .................. 435/252.1; 422/102; 435/288.3; 435/305.4
[58] Field of Search ................... 422/101, 102; 435/288.3, 305.4, 252.1, 174; 424/93

[56] References Cited

U.S. PATENT DOCUMENTS

| | | | |
|---|---|---|---|
| 3,055,808 | 9/1962 | Henderson | 435/298 |
| 3,158,553 | 11/1964 | Carski | 435/298 |
| 3,709,395 | 1/1973 | Brennan et al. | 215/38 R |
| 4,121,525 | 10/1978 | Courtis | 435/299 |
| 4,280,002 | 7/1981 | Bailey et al. | 435/298 |
| 4,299,921 | 11/1981 | Youssef | 435/298 |
| 4,358,908 | 11/1982 | Song | 47/66 |
| 4,670,398 | 6/1987 | Song | 435/305.4 |
| 5,324,636 | 6/1994 | Bartos et al. | 435/305.4 |

OTHER PUBLICATIONS

Poinar, "Entomophagous Nematodes", Progress in Zoology, vol. 32, (1986), pp. 95–120.

*Primary Examiner*—David A. Redding
*Attorney, Agent, or Firm*—Sughrue, Mion, Zinn, Macpeak & Seas

[57] ABSTRACT

Entomopathogenic nematodes are cultured in a culture vessel comprising a tray with side walls and an overlapping lid, also with side walls. A gasket of polyether polyurethane foam is positioned around the inside edge of the lid, preferably in a gutter formed by the walls of the lid and inclined flanges attached to the lid. Preferably the lid has apertures in it, closed with resilient seals. Stop members, mounted on the inside faces of the walls of the tray, prevent forced movement of the lid towards the tray when the flanges bear against the stop members, thus enabling the culture vessels to be stacked on each other without over-compression of the foam gasket. A method of rearing nematodes using such a culture vessel involves coating a layer of crumbed foam in the tray with an offal homogenate, closing the culture vessel, autoclaving it, inoculating the coated foam with the appropriate symbiotic bacterium, incubating this bacteria at about 23° C., inoculating the contents of the culture vessel with a monoxenic suspension of nematodes, incubating the nematodes at about 23° C. for a time to enable infective juvenile (J3 stage) nematodes to be produced in large quantities, then harvesting the J3 stage nematodes. A method and apparatus for harvesting nematodes, a vessel for incubating nematodes for use as an inoculum, and a method of separating J3 stage and adult nematodes are also described. The culture vessel can also be used to culture fungi, protozoa, bacteria and tissue cultures.

9 Claims, 3 Drawing Sheets

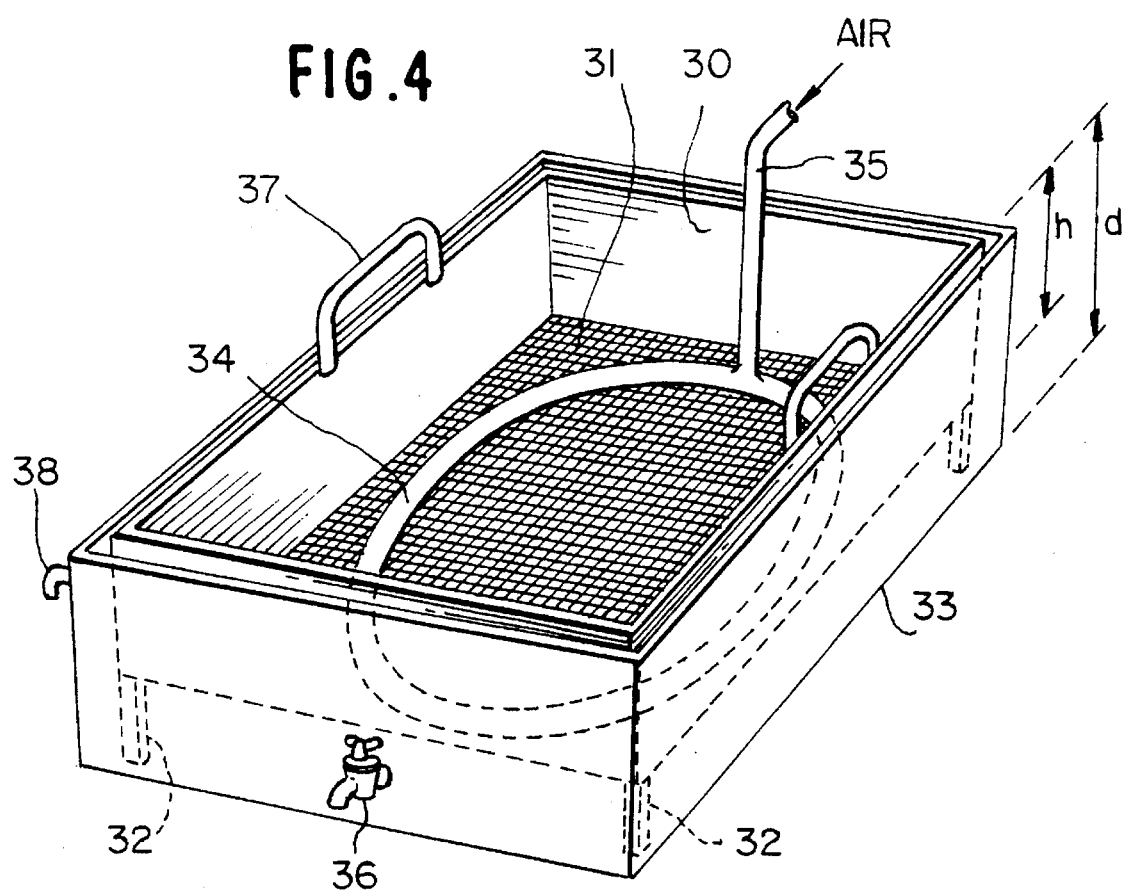
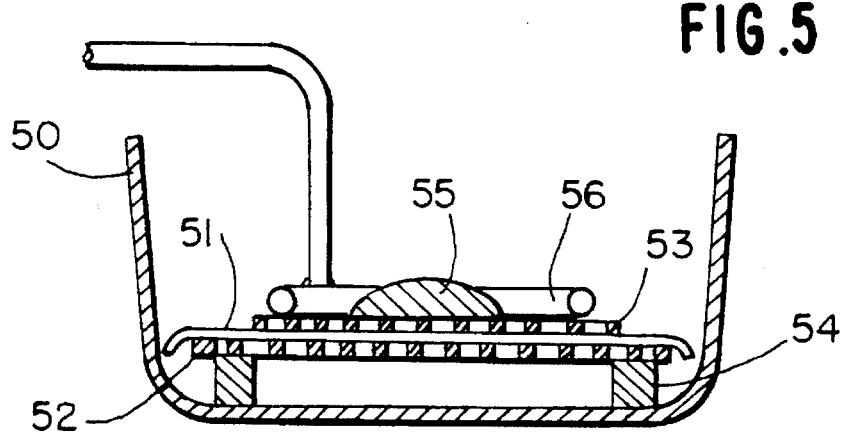

APPARATUS AND METHOD FOR REARING NEMATODES, FUNGI, TISSUE CULTURES AND THE LIKE, AND FOR HARVESTING NEMATODES

This is a Continuation of application Ser. No. 07/955,899 filed Dec. 11, 1992 now abandoned.

TECHNICAL FIELD

This invention was developed to facilitate the mass rearing of entomopathogenic nematodes in a solid culture, and their subsequent harvesting. However, the culture vessel form of the invention may also be used to rear other forms of nematodes, insect pathogenic fungi, protozoa, bacteria, tissue cultures and the like. In view of the historical association of the invention with the production of entomopathogenic nematodes, this aspect of the present invention will be given prominence in the following description of the invention.

BACKGROUND TO THE INVENTION

The rearing of nematodes for use in the control of insects and the like was initially effected by culturing the nematodes in their insect host. That was a slow and expensive method of production. A significant improvement in the culturing technology (resulting in reducing the production cost to about one hundredth of the previous cost) is described in the specifications of U.S. Pat. Nos. 4,178,366 and 4,334,498 to R. A. Bedding, and in the specification of the corresponding Australian patent No. 509,879. Those specifications describe three-dimensional in vitro monoxenic culturing techniques which utilise a large surface area and ample interstitial space of a culturing stack. Briefly, those in vitro techniques involve either cutting animal tissues into suitably sized pieces and stacking them appropriately, or forming a stack of inert materials and coating it with an homogenate. The stack so produced is then sterilised by autoclaving and the crude basic medium is made suitable for nematode nutrition and reproduction by culturing the nematode's special symbiotic bacterium (Xenorhabdus sp.) on the medium surface.

The techniques developed by R. A. Bedding, particularly the techniques described in his paper entitled "Large Scale Production, Storage and Transport of the Insect-parasitic Nematodes Neoaplectana spp. and Heterorhabditis spp", which was published in the *Annals of Applied Biology*, volume 104, pages 117–120, 1984, are very effective. However, the rapid increase in the demand for commercial quantities of entomopathogenic nematodes has revealed the need for a more suitable technique for producing the large quantities of nematodes required for, for example, the treatment of large areas of crops.

Hitherto, the commercial production of nematodes, using a technique described by Bedding in the *Annals of Biology* paper referred to above, has involved the following sequential steps.

1. Autoclavable polypropylene tubing is sealed with an impulse sealer to make a bag. Autoclave tape is applied over both sides of all seals to provide a bag of adequate strength. Air inlet and outlet tubes are introduced through the tape-reinforced seams and are cemented into place using a silicone rubber solution. A strip of autoclave tape is located centrally on the bag for use as an inoculation panel.

2. Between 3 and 5 kg of waste polyether polyurethane foam is made into crumbs and coated with an homogenate of chicken offal. The polypropylene bag is filled with this medium (during the filling operation the mouth of the bag must be kept clean). The bag is then sealed and the medium is distributed so that it forms an even thickness in the bag. Air is then evacuated from the bag, to enable sterilisation of the medium in minimal time, and the bag is wrapped in hessian, then placed flat in an autoclave. The hessian prevents local burning of the polypropylene bag material.

3. The bag is autoclaved at 121° C. (or at a slightly higher temperature) for a period of from about 75 minutes to about 90 minutes.

4. After cooling for several hours, the bag is placed in a laminar air flow sterile box, then inoculated with a broth suspension of bacteria. The inoculation is usually effected using a small sterilised funnel which is inserted through a slit in the innoculation panel. After adding the bacterial suspension, the slit is sealed using silicone rubber solution and the bag is left for 30 minutes to allow the silicone rubber solution to set.

5. When the silicone solution has set, the bag is kneaded and turned for several minutes to spread the bacterial suspension throughout the medium.

6. The bag is then placed in a constant temperature room, where air is supplied to the interior of the bag through the inlet and outlet tubes, the air being supplied through bacterial filters. After monitoring the air flow for a few hours to ensure that the bag is not over-inflating, the bag is left with the filtered air passing through it for four to five days, to incubate the bacteria.

7. At the end of the incubation period, the bag is inoculated with a nematode culture. The inoculation is effected by pouring the contents of three or four 500 ml flasks of mature nematode culture medium into the bag under sterile conditions, and distributing the culture medium over the surface of the bag contents without undue mixing. Normally the sterile conditions are ensured by performing the inoculation within a laminar air flow through a sterile box after the bag has been thoroughly sprayed with alcohol. The inoculation panel is slit so that a 5 cm diameter funnel tube can be inserted into the slit. The solid culture medium is shaken via the funnel tube into the bag, care being taken to direct the inoculum as widely as possible over the fresh bag medium surface. After the inoculation, the slit is sealed with silicone rubber solution and extreme care is taken during the next 30 minutes to avoid disturbing the slit until the rubber solution has set.

8. When the rubber solution which is sealing the inoculation slit has set, the bag is again connected to the air supply via bacteriological filters. After again observing the bag to ensure that the correct air supply rate has been established, the bag is left in a constant temperature room for two to three weeks.

9. The nematodes are then harvested from the bag by emptying the contents of the bag into a sieve having a floor of fine stainless steel mesh. The sieve containing the culture medium is placed in a slightly larger tray and the culture medium is covered with water for about two hours. During this time, the nematodes leave the culture and go into suspension in the water. The contents of the sieve are then rejected and the liquid remaining is pumped into a settling tank, where the nematodes are repeatedly sedimented and the washing water is decanted. Each bag that undergoes this treatment yields about 0.5 kg of nematodes, together with some debris, provided no bacteria from outside the bag environment have entered the bag after the autoclaving step. The presence of such foreign bacteria will severely reduce the yield of nematodes, and could cause a negligible yield.

The disadvantages of this technique include (a) the need for a fresh bag to be constructed for each culture;

(b) the requirement for at least two bacterial filters (which are not inexpensive) for each bag (although they can be reused 3 times);

(c) the considerable time that is required for the steps of (i) filling and sealing the bags (which ought to be conducted with two operators), (ii) the evacuation of air, (iii) the inoculation with both bacteria and nematodes, and (iv) waiting for the silicone rubber seal to dry;

(d) the inoculation dispersal is not efficient;

(e) the bags can be rendered useless by blockages in the filters (which occur ocassionally despite monitoring of the inflation and re-inflation of the bags) or by the failure of the electricity supply to the pumps which pump the air through the filters;

(f) the inflation of the bags results in a considerable reduction of the basal surface area unless the bag is held flat with weights; since the depth of the medium in the centre of each bag should not exceed 10 cm, this means that a reduced quantity of medium can be contained in each bag;

(g) there is an uneconomical use of space due to (i) the fact that the inflated bags take up many times the storage volume of the actual culture medium and (ii) the necessity of ready access to all bags for adjustment of air flows;

(h) the bags require suitable shelving to hold them, so that either a supply of air ducted to all shelf areas or a separate air pump for each bag must be provided; and (i) air pump maintenance and replacement is a significant expense.

Despite these disadvantages, sufficient nematodes for large scale field trials of up to 50 hectares, requiring the yield of at least two bags per hectare, can be produced. However, the production of sufficient nematodes to treat a commercial crop of thousands of hectares is unlikely to be technically feasible using this technique.

DISCLOSURE OF THE PRESENT INVENTION

A major objective of the present invention is to provide apparatus for use in the cultivation of entomopathogenic nematodes of the families Steinernematidae and Heterorhabditidae, other entomopathogenic nematodes, and a range of other organisms (including fungi and tissue cultures), in large quantities, reliably and at low cost.

This objective is achieved by constructing a culture vessel or cell from a large tray with a lid which provides a bacterial seal, and with the ability for sufficient air to move into and out of the tray that the oxygen levels within the culture vessel are maintained above about 12 percent and the carbon dioxide levels within the culture vessel do not exceed about 10 percent. In addition, the vessel or cell must be constructed so that the medium in the vessel does not dry out to any significant extent, and it is possible to add a bacterial suspension and a nematode culture (or the like) to the tray without the risk of contamination entering the culture vessel.

The present inventors have discovered that a self-aerating tray having these features can be produced if the tray is provided with an overlapping lid and with a compressible gasket of medium density polyether polyurethane foam (or a similar material) forming a partial seal between the lid and the tray. The present inventors have also found that, when using such a self-aerating tray, it is preferable for the lid to be provided with at least one (and preferably two or more) apertures which are closed by seals made from a rubber composition, neoprene or similar flexible and resilient autoclavable material, through which an inoculum can be injected into the tray.

The discovery that a gasket of polyether polyurethane foam prevents bacterial contamination of the inside of the cell was a surprising discovery. Cotton wool is commonly used for plugging culture flasks but its structure does not permit sufficient gas flow through it for cotton wool to be used in the present invention, although contaminating bacteria and fungal spores can traverse a cotton wool plug. Polyether polyurethane foam contains channels within it which have diameters many hundreds of times larger than bacterial cells. It is thought that possibly electrostatic forces within the foam are effective to restrain the movement of bacteria and fungal spores through the channels in the foam. The overlap (the lid is required to have an edge) is also believed to be important in maintaining gas flow and sterility.

It has been found by the present inventors that contamination of the contents of the culture vessel can occur when the lid is removed from the tray to add a bacterial broth or a nematode culture or the like. To avoid this type of contamination, the present inventors modified the lid of the culture vessel to include at least one aperture in the lid, the (or each) aperture being closed with a resilient seal that can be penetrated with a needle. It is then possible to sterilise the outside of the seal or seals with alcohol and to penetrate the (or each) seal with a sterilised hollow needle or canula to inject the bacteria or nematodes or the like into the tray. Removal of the canula does not destroy the sterile conditions because the natural resilience of the material of the seal effectively closes the needle-hole. Preferably the (or each) seal is a grommet-type seal.

Thus, according to the present invention, a culture vessel for the rearing of infective juvenile entomopathogenic nematodes, fungi, tissue cultures and the like comprises (a) a substantially flat tray having a continuous wall or a plurality of contiguous walls extending substantially orthogonally from the periphery of said tray;

(b) a substantially flat lid having essentially the same shape as said tray but dimensions greater than said tray, so that when said lid is positioned to cover said tray, the periphery of said tray is outside said wall or walls; said lid having a continuous side wall or a plurality of contiguous side walls which extend substantially orthogonally from the periphery of said lid; and (c) a gasket of medium density polyether polyurethane foam (or a similar foam material) positioned around the edge of said lid within and immediately adjacent to said lid side wall or walls, whereby, when said lid is placed on said tray, said gasket is contacted by the upper edges of the tray wall or walls.

Preferably, as indicated above, at least one grommet-type seal of autoclavable rubber compound, neoprene or the like is mounted in the lid.

Typically, the tray wall or walls will have a height of about 12 cm, the lid periphery will be approximately 1 cm outside the tray wall or walls, the tray side wall or walls will have a height of about 6 cm, and the gasket will have a width of about 4 cm. However, these dimensions may be substantially varied, to suit the convenience of the user of the culture vessel.

The tray (and therefore the lid) may have any desired shape. A circular or elliptically shaped tray will have a single wall extending from its periphery, and a similarly shaped lid will also have a single side wall. However, triangular, rectangular or other polygonally shaped lids and trays will each have a plurality of contiguous linear walls extending from their peripheries. Normally, for convenience in handling and storage, the tray and lid will have a rectangular shape.

Preferably the lid is provided with an inclined flange mounted on the face of the lid from which the side wall or walls of the lid extend. Such a flange will be substantially parallel to the side walls of the lid, with the edge of the flange which is remote from the lid surface being spaced from the edge of the lid a distance slightly less than the width of the gasket. In a typical culture vessel, this will be a distance of about 6 cm. Such a flange forms, with the side walls of the lid, a gutter around the periphery of the lid. The foam gasket can then be retained in the gutter by the resilience of the foam material and need not be stuck to the surface of the lid.

Since it will be convenient to have a culture vessel which can be stacked, the tray may be provided with a number of internal brackets or blocks. Each such bracket or block establishes a rigid internal stop member near the top of the walls of the tray. When the culture vessels are stacked, the weight of the overlying culture vessels on the lids of the lower culture vessels will compress the foam gaskets of the lower culture vessels until the internal flange on the lid of each of the lower culture vessels in the stack contacts the stops provided by the respective stop members. The stop members then prevent further compression of the foam gaskets.

The present invention also encompasses a method of rearing nematodes in the culture vessel of this invention.

Hence, according to the present invention, there is also provided a method of rearing infective juvenile entomopathogenic nematodes which comprises the sequential steps of:

(a) coating crumbed polyether polyurethane foam (or similar material) with an offal homogenate, and distributing the coated, crumbed foam evenly over the base of a tray of a culture vessel constructed in accordance with the present invention, then placing the lid of the culture vessel over the tray so that the foam gasket thereof is in contact with the entire top of the wall or walls of the tray;

(b) autoclaving the culture vessel and its contents at a temperature of about 121° C. for about 1 hour;

(c) allowing the autoclaved vessel to cool;

(d) inoculating the autoclaved foam and homogenate with the primary form of the symbiotic bacterium, Xenorhabdus sp., of the entomopathogenic nematode species to be cultured;

(e) maintaining the culture vessel and its contents at a temperature of about 23° C. for a period sufficient to incubate the symbiotic bacteria;

(f) inoculating the contents of the culture vessel with a monoxenic suspension of nematodes;

(g) maintaining the culture vessel at a temperature of about 23° C. for a period sufficient to enable the nematode species to reproduce and generate infective juveniles (J3) of the nematode species; and (h) harvesting the juvenile entomopathogenic nematodes from the culture vessel.

Embodiments of the culture vessel, the method of bulk rearing of J3 stage nematodes, and also of apparatus for and a method of harvesting infective juvenile (J3 stage) entomopathogenic nematodes, a cultivation vessel for conveniently producing an inoculum of nematodes, and a new method of separating adult and J3 nematodes, will now be described, by way of example only, with reference to the accompanying drawings.

BRIEF DESCRIPTION OF THE DRAWINGS

FIG. 4 is a perspective sketch of one form of apparatus used to harvest cultured nematodes.

FIG. 5 is a schematic sectional view through an assemblage of components in a container, for performing the separation of juvenile J3 nematodes from adult nematodes in a suspension of nematodes.

DETAILED DESCRIPTION OF THE ILLUSTRATED EMBODIMENTS

Figure 1:
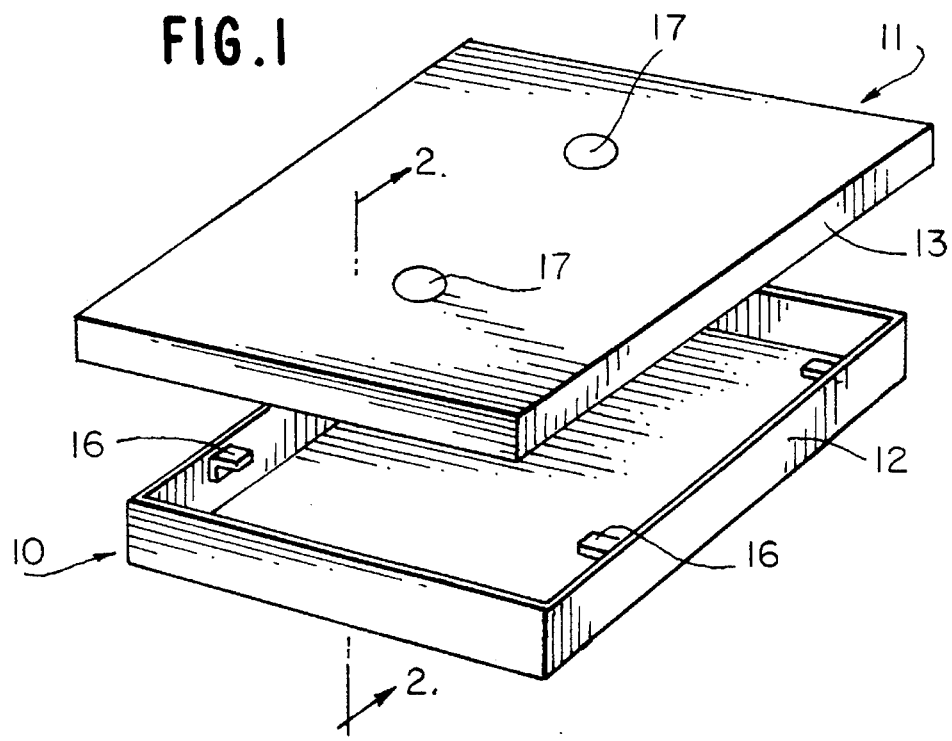
FIG. 1 is a perspective sketch of an embodiment of the culture vessel of the present invention, with the lid opened.
Figure 2:
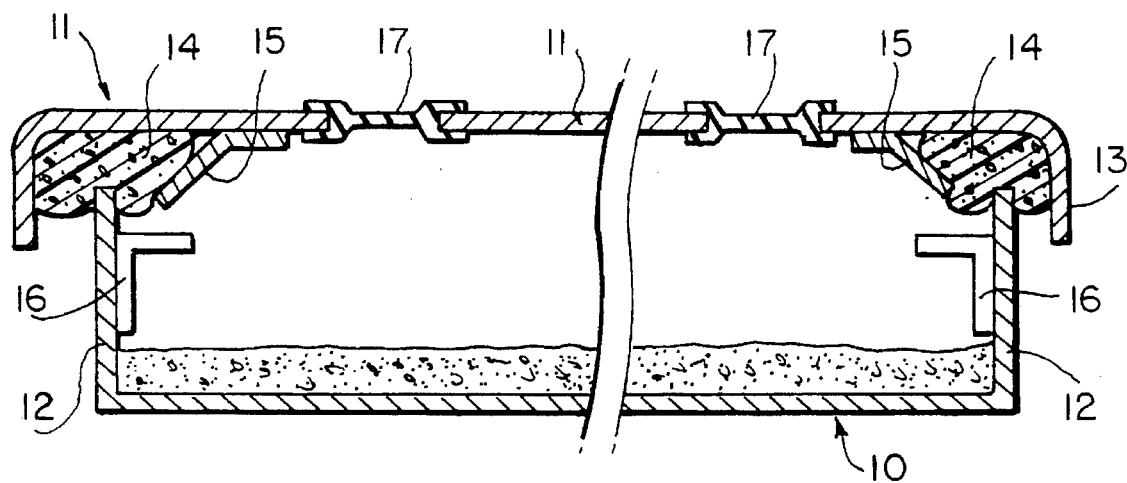
FIG. 2 is a sectional view at 2—2 of the vessel of FIG. 1, with the lid of the culture vessel in its closed position.

The culture vessel illustrated in FIGS. 1 and 2 consists of a rectangular tray 10 and a lid 11. The lid 11 is adapted to fit over, and overlap the edges of, the tray 10. The tray has vertical walls 12. The lid has side walls 13 extending orthogonally from it and a pair of grommet-type seals 17 mounted in respective circular apertures in the lid. As shown particularly in FIG. 2, each grommet-type seal has a relatively thick annular or toroidal edge region with a continuous groove formed in the outer surface of the edge region. This continuous groove receives, in a low pressure gas-tight sealing manner, the material of the lid 11 which is adjacent to the edge of a respective circular aperture formed in the lid. Each grommet-type seal also has a relatively thin, circular, centre region. Normally the edge region and the centre region of a grommet-type seal are formed integrally, from a resilient autoclavable material such as neoprene or a suitable rubber composition. The grommet-type seals are optional, but are preferred.

When the lid 11 is placed over the tray 10, to form a culture vessel, a gasket 14 of medium density polyether polyurethane foam forms a "seal" between the lid and the top of the tray walls 12. As noted above, the seal is not an airtight seal but allows gas to move into and out of the culture vessel. Other resilient foamed materials may be used for the gasket 14 instead of medium density polyether polyurethane foam.

The lid 11 of the embodiment illustrated in FIGS. 1 and 2 is provided with a flange 15 which extends from the face of the lid from which the side walls 13 project. The flange 15 preferably extends completely around the lid, a short distance in from the outer edge of the lid. The flange 15 shown in FIG. 2 is at an acute angle to the plane of the lid. The flange 15 and the side walls 13 form a gutter which serves to hold the foam gasket 14 in position alongside the side walls 13. The natural resilience of the foam material retains it in the gutter, thus avoiding the need to glue the gasket 14 to the lid. However, spots (or a strip or a layer) of an adhesive material may be used, if desired, to retain the gasket in place. Indeed, in the absence of the inclined flange 15, a small quantity of an adhesive material will normally be used to hold the foam gasket in its required position alongside the side walls 13.

A number of culture vessels were constructed to test the present invention. Some of the lids of the culture vessels had no grommet-type seal 17. Other culture vessels were constructed with lids having the seals 17 as shown in FIGS. 1 and 2. All of the culture vessels had rectangular trays and lids. Two sizes of prototype culture vessels were fabricated. The larger culture vessels had trays 75 cm long, 45 cm wide and 12 cm deep; the smaller culture vessels had trays 45 cm long, 38 cm wide and 12 cm deep. The lids measured 78.5 cm by 47 cm for the larger trays, and 48.5 cm by 40 cm for the smaller trays, with side walls extending 6.5 cm from the lid. In all instances, the foam gasket had a width of 5 cm and a thickness of 3 cm. These dimensions are, of course, variable.

Some of the trays of the prototype culture vessels were provided with four brackets 16 mounted on the insides of two of the tray walls 12, as shown in FIGS. 1 and 2. The brackets 16 act in conjunction with the inclined flange 15 to prevent the foam gasket being crushed or compressed to an unacceptable extent when a number of the culture vessels are stacked one on top of the other. The lower edge of the flange 15 contacts the upper surface of the brackets 16 when a predetermined maximum compression of the foam gasket has been effected. Further compression of the gasket material cannot then occur. Of course, if it is not proposed to stack the trays on each other, the brackets 16, or blocks or stops of other shapes mounted on the walls 12 to perform the same function as the brackets 16, will not be required.

The prototype trays and lids, and the flanges 15 and brackets 16, were made of aluminium, but other suitable materials, including plastics materials, may be used to construct a culture vessel.

The first batch of prototype culture vessels, as indicated above, had lids which were not provided with the grommet-type seals 17. In about 1,000 trials with those first prototype culture vessels, contamination of the medium within a tray occurred on two occasions, despite very careful handling in a supposedly clean, laminar air-flow environment. Such a low incidence of contamination demonstrates the ability of the foam gasket to provide an effective seal against the intrusion of bacteria and fungal spores. However, the fact that contamination did occur on those two occasions shows that if less sterile external conditions than those created by the present inventors may exist during the mass production of nematodes, it would be unwise to remove the lid of the culture vessel completely to add bacterial broth and nematode cultures. Hence the grommet-type seals were conceived and adopted in the second batch of prototype culture vessels.

To use the prototype culture vessels of the present invention to produce infective juvenile nematodes, the following procedure, which illustrates the method of the present invention, has been adopted.

Step 1

Crumbed polyether polyurethane foam is coated with offal homogenate, using the method described in the aforementioned *Annals of Applied Biology* paper by R. A. Bedding.

Step 2

Between 2 and 3 kg of the coated, crumbed foam is loaded into each tray and distributed evenly over the base of the tray to a depth of about 8 cm. (The depth of this layer is an important parameter; with trays having areas larger or smaller than the area of the prototype trays, different masses of the coated, crumbed foam will be used.)

Step 3

The lids (with their foam gaskets) are placed on the trays, which are then autoclaved at a temperature of about 121° C. for one hour. Several trays may be stacked one on another during this autoclaving, provided spacers about 2.5 cm thick are used to separate the trays to allow for steam circulation around each tray.

Step 4

After cooling, the trays are inoculated with the primary form of the symbiotic bacterium, Xenorhabdus sp., of the entomopathogenic nematode to be cultured.

If the lid of the culture vessel is not provided with grommet-type seals, the inoculation is effected within a cabinet through which there is a laminar flow of clean (sterile) air, after the outsides of the trays and lids have been thoroughly sprayed with 90 percent ethyl alcohol (for sterilisation). Each tray lid is lifted vertically off its tray and one end of the tray lid is rested on a ledge (a 2.5 cm wide ledge in the equipment used by the present inventors) which is fixed to the upper side wall of the laminar flow cabinet. The other end of the lid is supported at its mid-point by a hook suspended from the cabinet ceiling. This support procedure for the lid maintains its sterility while allowing ready access to the tray. About 300 cc of a nutrient bacterial broth (for example, a yeast salts (YS) broth in which symbiotic bacteria have been incubated for 24 hours) is then sprinkled as evenly as possible over the surface of the coated, crumbed foam, which now resembles a sponge. This "sponge" is then raked over with a sterile implement to ensure that the bacteria are spread to all the crumbs of the foam. The lid is then replaced on the tray.

If the culture vessel has a lid which is fitted with two grommet-type seals, the inoculation is effected in the following manner. First, the outside of the seals and the surrounding regions of the lid are sprayed with alcohol, and a flame is applied to a canula (hollow needle) which is connected to a supply of a broth of the symbiotic bacteria. The sterile canula is pushed through one of the sterilised seals and about half of the broth is injected into the tray. Subsequently, the sterile canula is pushed through the other sterilised seal and the remainder of the broth is injected into the tray. Movement of the canula during the injection of the broth ensures that it is evenly distributed over the crumbed foam in the tray. It is not necessary for the injection of the broth to be carried out with the tray inside a laminar air flow cabinet. About 300 cc of the nutrient bacterial broth (for example, a yeast salts (YS) broth in which the symbiotic bacteria have been incubated for 24 hours) are sprayed over the surface of the coated, crumbed foam, in this manner. At this time, the foam resembles a sponge. If desired, the tray may be shaken at this point to ensure that the bacterial broth is evenly distributed over the tray.

Step 5

The culture vessel (the tray and its lid) is then moved to a constant temperature region where it is maintained at a temperature of about 23° C. for about four days to incubate the symbiotic bacteria. This incubation time may be varied depending upon the bacteria species involved. In some circumstances this bacterial incubation step may be omitted.

Step 6

The tray is next aseptically inoculated with entomopathogenic nematodes. The inoculation is carried out using the technique described in step 4 above, but with the bacterial broth replaced with a suspension in water of nematodes (almost entirely juvenile nematodes) which have been aseptically harvested. Care must be taken to distribute the inoculated nematodes as evenly as possible over the surface of the medium in the tray.

Step 7

The tray is then removed to a constant temperature region where it is maintained at a temperature of about 23° C. for a predetermined period. This period depends upon the species of nematode being grown. In the case of Steinernema species, the infective juveniles develop in 14 days. In the case of Heterorhabditis species, this incubation period is from 21 to 28 days.

Step 8

The J3 stage entomopathogenic nematodes are then harvested from the trays.

To cultivate the inoculum of entomopathogenic nematodes used in Step 6 above, a novel cultivation vessel has been devised by the present inventors.

This cultivation vessel comprises a rectangular tray in which is located a rectangular inner tray having a stainless steel seive as its base. The inner tray has contiguous walls extending orthogonally from its base and a pair of handles. Each handle comprises a cross-member which connects a pair of side arms. Each side arm is pivotally connected to a respective side wall of the inner tray at a point a distance from the end of the side wall, so that it is moveable in a plane which is parallel to the side walls of the inner tray. Each side arm extends below its respective pivot point a distance such that if the cross-members are moved towards the centre of the inner tray, the lower ends of the side arms are positioned above the level of the base of the inner tray; but if the cross-members are moved away from the centre of the inner tray, the lower ends of the side arms project below the level of the base of the inner tray, so that the lower end regions of the side arms act as spacers or legs for the inner tray.

Figure 3:
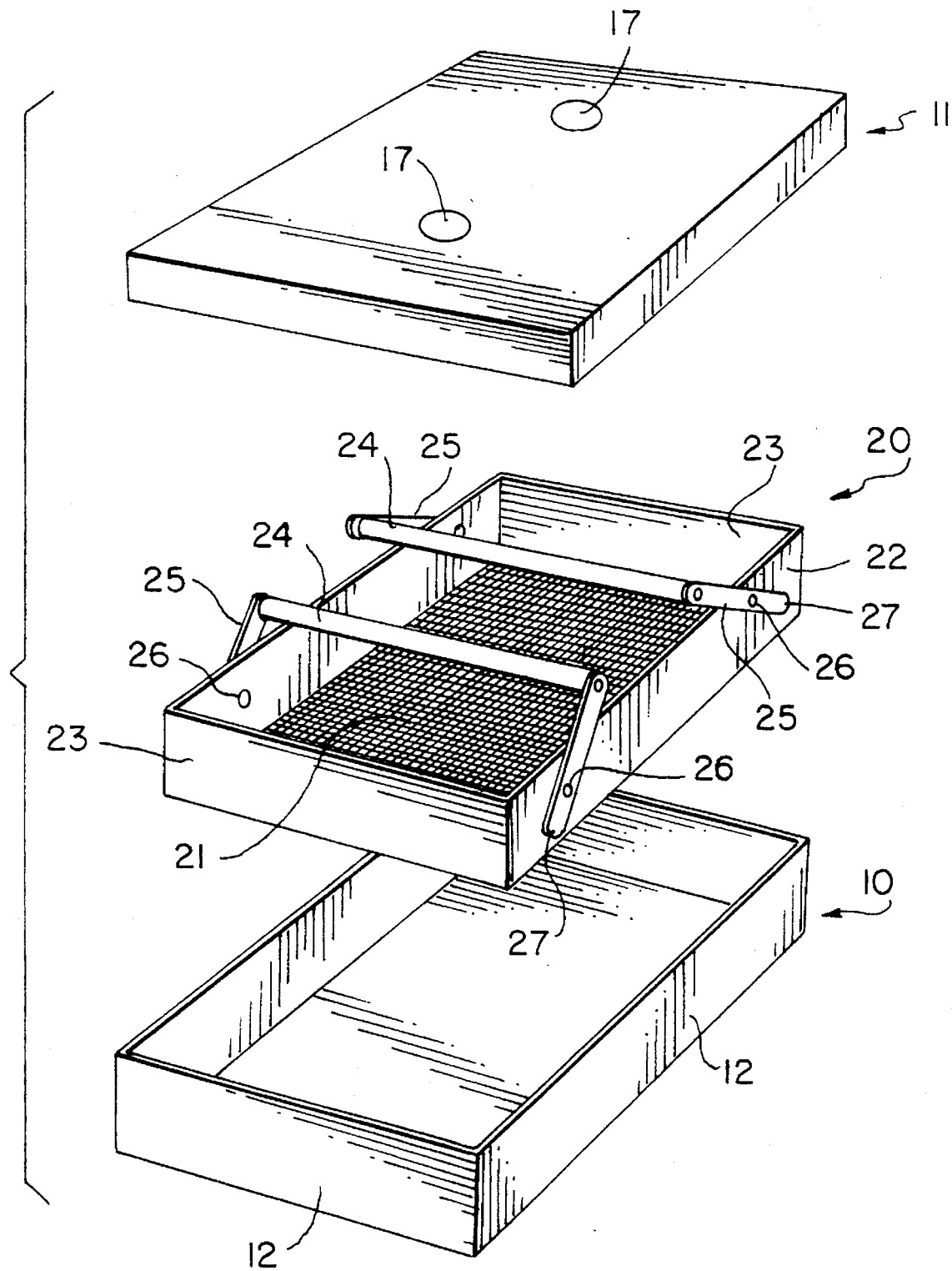
FIG. 3 is a perspective sketch, showing the components of the preferred form of the cultivation vessel for preparing an inoculum of nematodes for use in the bulk rearing method of the present invention.

An embodiment of this cultivation vessel is illustrated in FIG. 3, which clearly shows its three main components—a tray 10, a lid 11 and an inner tray 20. The lid 11 is essentially the same as the lid 11 of FIGS. 1 and 2. The tray 10 is similar to the tray 10 of FIGS. 1 and 2, but it has higher walls 12 and it does not feature the brackets 16. The inner tray 20 has a steel mesh (sieve) base 21, side walls 22 and end walls 23. A pair of handles have cross-members 24 and side arms 25. The side arms 25 are pivotally connected to the side walls 22 at pivot points 26. As shown in FIG. 3, the pivot points 26 are not at the ends 27 of the side arms 25, but are at a distance from the ends 27 such that when the cross-members are in the position shown in FIG. 3 (that is, over the central region of the inner tray 20), the ends 27 of the side arms 25 do not project below the level of the base 21. However, if the cross-members 24 are moved to a position where they are above the end walls 23, the ends 27 of the side arms are below the level of the base 21, and the side arms effectively provide legs for the inner tray.

When used to culture nematodes (or the like), the handles are moved to their most central positions, where the cross-members 24 (or suitably located stops mounted on the side arms 25) come into contact with the top edges of the side walls 22. In this position, the handles may perform the same function as the stops or brackets 16 which are preferably mounted on the walls 12 of the tray 10 of the culture vessel of the present invention which is illustrated in FIGS. 1 and 2.

To rear entomopathogenic nematodes using the cultivation vessel of FIG. 3, the same procedure as that outlined above is adopted, except that the crumbed, coated foam is loaded into the inner tray, which is positioned within the tray 10 with the base 21 of the inner tray resting on the base of the outer tray 10.

A number of prototype cultivation vessels of the type shown in FIG. 3 have been constructed and tested. In no instance has any contamination affected the rearing of nematodes in such prototypes.

To aseptically harvest the nematodes reared in the cultivation vessel of FIG. 3 for use as an inoculum, the cultivation vessel is placed in a laminar air flow cabinet and after the outsides of the outer tray and the lid (including the underside of the overlapping region of the lid) have been sprayed with alcohol (normally, 90 percent ethyl alcohol is used for sterilisation), the lid 11 is removed from the culture vessel. The cross-members 24 of the handles of the inner tray 20 are then moved to a position substantially above the end walls 23 of the inner tray, so that the mesh base 21 of the inner tray is above the base or floor of the tray 10. Sterile water is then added to the tray 10 until the foam in the inner tray is completely covered to a depth of about 15 cm.

The water-covered foam is allowed to stand for about two hours. During this time the nematodes in the culture medium (the foam) leave the medium and move into the water, which thus becomes a suspension of adult and juvenile nematodes.

The inner tray or seive 20, with the culture medium, is then removed from the tray 10 to leave the suspension of entomopathogenic nematodes in the tray 10. This liquid is poured into a sterile bowl where the nematodes are washed with sterile water using a sedimentation and decanting procedure. The washed sediment of nematodes, containing about 100,000 nematodes per milliliter, is then poured into a sterile flask, from which the nematodes can be used as an inoculant.

The aseptic harvesting of the nematodes reared in bulk in the culture vessels of the present invention, as illustrated in FIGS. 1 and 2, can be effected in the conventional manner, which involves spreading a thin layer of the culture medium containing the nematodes over a sieve and covering the layer of culture medium with water. Nematodes move from the culture medium into the water, then fall through the sieve to be collected in a tray having side walls, on the base of which the sieve is standing. The discussion, above, of the previously used technique for producing nematodes outlined this harvesting technique.

This harvesting technique, however, is time and space consuming and a new extraction technique for nematodes has been developed to complement the apparatus and rearing method of the present invention. The new extraction technique, which is not restricted in its use to the harvesting of nematodes cultured using the method described above or the apparatus of FIGS. 1 and 2, involves deep tank extraction.

The equipment illustrated in FIG. 4 has been developed for this deep tank extraction technique. This equipment includes a sieve in the form of a rectangular tray having walls 30 and a steel mesh base 31, supported on legs 32. The sieve stands in a tank 33. In prototype harvesting equipment constructed by the present inventors, the tray, the legs and the tank were constructed of aluminium, but it will be appreciated that any other suitable material may be used for these components. The prototype harvesting equipment has the following dimensions (which are exemplary only, and not limiting):

sieve wall height (h)—20 cm;

sieve base 31 dimensions—68 cm by 42 cm;

length of the legs 32—8 cm;

tank 33 rectangular dimensions—72 cm by 45 cm; and tank wall height (d)—30 cm.

A generally oval-shaped or elliptical tube 34 (of aluminium in the prototype equipment) is positioned on the steel mesh floor 31 of the sieve. Holes in this elliptical tube 34 (four holes in each side of the oval tube) act as air outlets from the tube. Air is supplied to the tube 34 through a pipe 35. It should be noted that the aeration tube need not be oval or elliptical; aeration tubes having other suitable shapes may be used.

To use this equipment to harvest nematodes, the natural nematode culture on foam from two culture vessels of the type illustrated in FIGS. 1 and 2 is loaded on to the mesh 31. The tank 33 is then filled with water until the water level is about 3 cm below the top of the tank walls. With this depth of water in the tank, the foam culture medium has been fully immersed in water. Air is then bubbled vigorously through the foam in the sieve from the outlets in the elliptical tube 34. After about 90 minutes of this aeration, the tube 34 is removed and the tank is left undisturbed for about 60 minutes. At the end of this time, at least 95 percent of the nematodes have formed a sediment at the bottom of the outer tank 33.

The foam and surplus water are then removed. A suction pump may be used to extract all material down to the floor of the sieve. Alternatively, a tap 36, positioned about 5 cm above the base of the tank 33, is opened to decant off most of the overlying liquid (which comprises water, various solutes and small particles of spent culture medium).

The sieve is then removed from the tank 33 and the foam is discarded, together with the other material remaining in the sieve. Water is added to the tank 30 and the nematodes are allowed to settle for about 45 minutes. The excess water is then decanted. The washing, settling and decanting operation is repeated until the nematodes are in a clean suspension. The exit and entry of the washing water is effected preferably using electronically controlled solenoid valves.

The aerating elliptical tube 34 is then placed on the floor of the tank 33 and air is bubbled through a suspension of the nematodes in water for at least two days. This aeration step ensures that most of the remaining culture medium is decomposed.

The nematodes are then finally washed and the sediment of nematodes is pumped from the tank 33 into sieves lined with a fine cotton or linen cloth through which water passes readily, but which the nematodes cannot penetrate. Surplus water still remaining can be removed by centering the edges of the cloth and squeezing the centred cloth manually, as in the manner used in some types of cheese making. The nematode cream thus produced may then be stored, preferably using the technique described in the specification of International patent application No PCT/AU88/00127, which is WIPO publication No WO 88/08668.

The nematodes harvested by each of the two harvesting techniques described above will comprise a mixture of adult nematodes and infective J3 juveniles. A further novel development in this field, namely a method of separating the juvenile nematodes from the adults and from any residual culture medium debris, will now be described.

This separation method uses the assembly shown in FIG. 5 within a container 50 (such as a bowl). This assembly comprises a layer of a cotton cloth material 51, sandwiched between two mesh screens 52 and 53, mounted horizontally. The lower mesh screen 52 is supported on blocks 54 above the floor of the container 50. The cotton cloth extends to the edges of the lower mesh screen 52, with a surplus of the cloth present at the edges of the upper mesh screen 53. Preferably the lower mesh screen is a seive of the type illustrated in FIG. 4. Indeed, the equipment illustrated in FIG. 4, with the addition of a cloth layer and a second mesh screen, may be used for this method of separating adult and juvenile (J3 stage) nematodes.

The nematode suspension 55 is placed on top of the upper mesh screen 53. Water is added to the container 50 until the suspension of nematodes is covered to a depth of about 15 cm. An aerator 56 of the type shown in FIG. 4 is then placed on the upper screen 53 and air is bubbled vigorously through the water for about 12 hours.

During this aeration period, the majority of the nematodes are in suspension. However, the swirling motion of the water is such that nematodes continuously fall, in small numbers, on the top mesh screen 53. When the infective juveniles fall on the top mesh screen 53, they move onto, then through, the cloth layer 51 and into the relatively calm water under the lower mesh screen 52, thus making a space for further nematodes to fall onto the top mesh screen 53. The adult nematodes appear to have insufficient energy to move through the mesh and cloth sandwich, and thus are carried into suspension again or remain on the top of the mesh screen 53.

The aeration is important when a substantial number of nematodes are subjected to this method of separation of adults from juveniles, for without aeration there would be insufficient oxygenation of the mass of nematodes and a lack of opportunity for many juveniles to reach the top mesh and migrate through the cloth layer.

After the aeration period, the mesh sandwich is removed—and with it the adult nematodes. The J3 juveniles are then allowed to settle. Finally, the nematodes are washed with sterile water using the usual sedimentation and decanting technique.

The nematode rearing, harvesting and separating techniques described above have been successfully tested with most of the known species of entomopathogenic nematodes including: *Steinernema feltiae* (previously known as *Neoaplectana bibionis;* for the purpose of this specification all reference to Steinernema is as a synonym of Neoaplectana), *Steinernema carpocapsae*, *Steinernema glaseri*, *Steinernema affinis*, *Steinernema anomali*, *Heterorhabditis heliothidis*, *Heterorhabditis bacteriophora*, *Heterorhabditis megidis*, and six further as yet undescribed new species of Steinernema from Australia, China and the USA, two new species of a new genus of steinernematid from Australia, and four as yet undescribed new species of Heterorhabditis from Australia, China, Cuba and Europe.

It will be appreciated by those skilled in this art that the nematode rearing apparatus of the present invention is also well suited to rearing other organisms. Among such other organisms are insect pathogenic fungi, protozoa and bacteria, as well as nematodes suitable for tropical fish food and nematode pathogenic fungi. Tissue cultures from a range of animals and plants, and viruses on such tissue cultures, may also be reared on a large scale using the apparatus of the present invention.

To further illustrate the present invention, a selection of examples of the production of entomopathogenic nematodes and insect pathogenic fungi will now be provided.

EXAMPLE 1

Over a period of two weeks, forty culture vessels of the type illustrated in FIGS. 1 and 2 were prepared as follows. For each culture vessel, 2000 g of chicken offal comprising intestines, hearts and livers, but not gizzards, were homogenized in a 5 liter Waring blender with 500 g water. This homogenate was evenly mixed, manually, with 180 g of crumbed polyether polyurethane foam so as to produce an as even as possible coating throughout all the interstices of the foam. The coated foam was then loaded at an even depth into the trays of the culture vessels and the culture vessels were autoclaved at about 121° C. for 1.5 hours. For inoculation of the culture vessels with nematodes and bacteria, fully sterile procedures were adopted. After cooling for several hours, each culture vessel was inoculated with symbiotic bacteria by the injection of 300 cc of a nutrient broth culture over the surface of the foam. The bacterial culture used was of *Xenorhabdus nematophilus* derived from the All strain of *Steinernema feltiae* which had been incubated at 28° C. for 24 hours.

Each culture vessel was then incubated at 23° C. for 5 days before being inoculated with nematodes. The contents of two monoxenic 500 ml flask cultures of *Steinernema carpocapsae* All strain were injected over the surface of the medium therein. (The cultures of inoculum were prepared in known manner on crumbed polyether polyurethane foam coated with chicken offal homogenate as described above for the culture vessels; bacterial inoculum was mixed into the foam/medium by shaking and the nematode inoculum was added from a mature flask culture 5 days later.) After distributing the nematode inoculum, no further mixing was attempted since mixing at this stage is known to be detrimental to the production of nematodes. The culture vessels were then incubated for 16 days at 23° C. and harvested as described above but with the contents of each culture vessel in a separate harvester. Yields ranged from 1000 million infective juvenile J3 nematodes per culture vessel to 2100 million infective juvenile J3 nematodes per culture vessel (the average being 1300 million J3 nematodes per culture vessel) with from 0.1 percent to 2 percent non-J3 stages present.

EXAMPLE 2

Ten culture vessels were prepared exactly as in Example 1, but the nematode culture was injected immediately after the bacteria. The average yield from these culture vessels was 1250 million J3 stage nematodes per culture vessel.

EXAMPLE 3

Eight culture vessels, prepared as in Example 1, were inoculated with *Xenorhabdus nematophilus* poinarii, incubated for 5 days and then each inoculated with the contents of two 500 ml cultures of Steinernema sp. strain NC 513. Cultures were harvested after two weeks and yields ranged from 1220 million to 1600 million infective juvenile (J3 stage) nematodes and averaged 1360 million J3 stage nematodes per culture vessel.

EXAMPLE 4

Ten culture vessels, prepared as in Example 1, were inoculated with *Xenorhabdus nematophilus* bovienii and five days later with *Steinernema feltiae*. Cultures were harvested after two weeks and yields ranged from 500 million to 1400 million (averaging 900 million) J3 stage nematodes per culture vessel.

EXAMPLE 5

Twenty culture vessels were prepared as in Example 1 but for each culture vessel there were 2000 g chicken offal, 285 g fat, 571 g water, on 209 g foam. 300 cc of a nutrient YS broth containing *Xenorhabdus luminescens* was used as a bacterial inoculum and after incubating at 23° C. for 5 days, two culture flasks of *Heterorhabditis heliothidis* C1 strain were added to each culture vessel. The culture vessels were incubated for 28 days and harvested as in Example 1. Yields ranged from 800 million to 1600 million (and averaged 1100 million) J3 stage nematodes per culture vessel.

EXAMPLE 6

Twenty culture vessels were prepared, inoculated and incubated as in Example 5 but Heterorhabditis sp NZ was used as the nematode inoculum. Yields ranged from 700 million to 1300 million (and averaged 950 million) J3 stage nematodes per culture vessel.

EXAMPLE 7

For the mass rearing of the insect pathogenic fungus *Metarrhyzium anisopliae*, one culture vessel containing 2 kg rice and 3 liters of water was autoclaved for 1.5 hours. After cooling the culture vessel, it was inoculated with rice culture of this fungus from a previously established culture. After two weeks, the tray lid was removed and the rice dried for several days, when some $10^9$ spores of fungus per gram of rice were available. The dried rice with Metarrhyzium spores was then utilized for introducing the fungus to insect populations.

EXAMPLE 8

A further culture vessel was prepared, inoculated and incubated in the same way as in Example 7 except that the rice was inoculated after autoclaving with the insect pathogenic fungus *Beauvaria bassiana*. Yields from this tray were similar to the yields obtained in Example 7.

I claim:

1. A culture vessel for the large scale rearing of infective juvenile entomopathogenic nematodes, fungi, and tissue cultures, said culture vessel comprising:
   (a) a substantially flat tray having a continuous wall extending substantially orthogonally from the periphery of said tray;
   (b) a substantially flat lid having essentially the same shape as said tray but dimensions greater than said tray, so that when said lid is positioned to cover said tray, a periphery of said lid is outside said wall; said lid having a continuous side wall which extends substantially orthogonally from the periphery of said lid;

said lid including at least one flange, said at least one flange extending from the same face of the lid as the side wall of the lid, said at least one flange being substantially parallel to the side wall of the lid and being inclined towards the side wall of the lid so as to form a gutter between said at least one flange and said side wall; said lid further provided with at least one aperture which is closed by a seal of a flexible, resilient, autoclavable material; and (c) an air permeable gasket of medium density polyether polyurethane foam positioned around the edge of said lid within said gutter and adjacent to said lid side wall, whereby when said lid is placed on said tray, said gasket is contacted by the upper edges of the tray wall.

2. A culture vessel as defined in claim 1, in which the or each aperture is a circular aperture and said seal is a grommet-type seal, said grommet-type seal having (i) a thick annular or toroidal edge region with a continuous groove formed in the outermost region thereof, said groove being adapted to receive the material of the lid adjacent to the edge of the aperture associated with the seal, and (ii) a thin, circular central region connected at its periphery to said annular edge region.

3. A culture vessel as defined in claim 1, in which said or each seal is made from a rubber compound or from neoprene.

4. A culture vessel as defined in claim 1, including a plurality of stop members affixed to the inside face of the wall of said tray, each stop member being so positioned that the edge of said or an associated flange extending from the lid bears against the stop member when the lid has been forced towards the tray and a predetermined compression of the gasket has occurred.

5. A culture vessel for the large scale rearing of infective juvenile entomopathogenic nematodes, fungi, and tissue cultures, said culture vessel comprising:

(a) a substantially flat tray having a plurality of contiguous walls extending substantially orthogonally from the periphery of said tray;

(b) a substantially flat lid having essentially the same shape as said tray but with dimensions greater than said tray, so that when said lid is positioned to cover said tray, a periphery of said lid is outside said walls; said lid having a plurality of contiguous side walls which extend substantially orthogonally from the periphery of said lid; said lid including at least one flange, said at least one flange extending from the same face of the lid as the side walls of the lid, said at least one flange being substantially parallel to the side walls of the lid and being inclined towards the side walls of the lid so as to form a gutter between said at least one flange and said side walls; said lid further provided with at least one aperture which is closed by a seal of a flexible, resilient, autoclavable material; and (c) an air permeable gasket of medium density polyether polyurethane foam positioned around the edge of said lid within and adjacent to said lid side walls, whereby, when said lid is placed on said tray, said gasket is contacted by the upper edges of the tray walls.

6. A culture vessel as defined in claim 5, in which said at least one aperture is a circular aperture and said seal is a grommet-type seal, said grommet-type seal having (i) a thick annular or toroidal edge region with a continuous groove formed in the outermost region thereof, said groove being adapted to receive the material of the lid adjacent to the edge of the aperture associated with the seal, and (ii) a thin, circular central region connected at its periphery to said annular edge region.

7. A culture vessel as defined in claim 5, in which said at least one seal is made from a rubber compound or from neoprene.

8. A culture vessel as defined in claim 5, including a plurality of stop members affixed to the inside face of the walls of said tray, each stop member being so positioned that the edge of an associated flange extending from the lid bears against the stop member when the lid has been forced towards the tray and a predetermined compression of the gasket has occurred.

9. A method of rearing infective juvenile entomopathogenic nematodes, said method comprising the sequential steps of:

(a) coating crumbed polyether polyurethane foam with an offal homogenate, and distributing the coated, crumbed foam evenly, to a depth of about 8 cm, over the base of a tray of a culture vessel constructed in accordance with any one of claims 1–8, then placing the lid of the culture vessel over the tray so that the foam gasket thereof is in contact with the entire top of the wall or walls of the tray;

(b) autoclaving the culture vessel and its contents at a temperature of at least 121° C. for about 1 hour;

(c) allowing the autoclaved vessel to cool;

(d) inoculating the autoclaved foam and homogenate with the primary form of the symbiotic bacterium, Xenorhabdus, sp., of the entomopathogenic nematode species to be cultured;

(e) maintaining the culture vessel and its contents at a temperature of about 23° C. for a period sufficient to incubate the symbiotic bacteria;

(f) inoculating the contents of the culture vessel with a monoxenic suspension of nematodes;

(g) maintaining the culture vessel at a temperature of about 23° C. for a period sufficient to enable the nematode species to reproduce and generate infective third stage juveniles of the nematode species; and (h) harvesting the juvenile entomopathogenic nematodes from the culture vessel.

* * * * *